(12) United States Patent
Pelrin et al.

(10) Patent No.: US 8,602,641 B2
(45) Date of Patent: Dec. 10, 2013

(54) ENVIRONMENTAL TEST SYSTEM AND METHOD WITH IN-SITU TEMPERATURE SENSING OF DEVICE UNDER TEST (DUT)

(75) Inventors: James Pelrin, Taunton, MA (US); Norbert W. Elsdoerfer, Warwick, RI (US)

(73) Assignee: Temptronic Corporation, Sharon, MA (US)

( * ) Notice: Subject to any disclaimer, the term of this patent is extended or adjusted under 35 U.S.C. 154(b) by 0 days.

(21) Appl. No.: 13/281,964

(22) Filed: Oct. 26, 2011

(65) Prior Publication Data

US 2013/0107906 A1    May 2, 2013

(51) Int. Cl.
*G01N 25/00* (2006.01)
(52) U.S. Cl.
USPC ............................................. 374/45
(58) Field of Classification Search
USPC ............................................. 374/45; 700/300
See application file for complete search history.

(56) References Cited

U.S. PATENT DOCUMENTS

| | | |
|---|---|---|
| 2006/0158207 A1 | 7/2006 | Reitinger |
| 2006/0254372 A1* | 11/2006 | Scott et al. .................. 73/865.6 |
| 2007/0023536 A1* | 2/2007 | Baston ........................ 236/44 C |
| 2012/0239220 A1* | 9/2012 | Wang ............................. 700/300 |

OTHER PUBLICATIONS

Melexis Microelectronic Integrated Systems, InfraRed Thermometer Family, examples: model No. MLX90614, MLX90615, www.melexis.com.
Micro IRt/c.4-K-440F/220C,The World's Smallest 4:1 Field of View Infrared Temperature Sensor, Exergen, Watertown, Massachusetts.
International Search Report and Written Opinion issued PCT Application PCT/US2012/062178 dated Feb. 6, 2013, 10 pages.

* cited by examiner

*Primary Examiner* — Lisa Caputo
*Assistant Examiner* — Jamel Williams
(74) *Attorney, Agent, or Firm* — Pierce Atwood LLP; Steven M. Mills

(57) ABSTRACT

An environmental chamber system and a method for testing a device under test (DUT) include an environmental chamber in which the DUT can be tested. A temperature sensor senses temperature of the DUT, the temperature sensor generating a signal indicative of temperature of the DUT. A controller receives at least one input signal related to at least one of temperature and humidity in the chamber and the signal indicative of temperature of the DUT and provides at least one control signal for adjusting at least one of temperature and humidity in the chamber, such that the temperature of the DUT is not below a dew point of an environment in the chamber in a region of the chamber near the DUT, such that condensation in the environment in the chamber in the region near the DUT does not occur.

13 Claims, 6 Drawing Sheets

ENVIRONMENTAL TEST SYSTEM AND METHOD WITH IN-SITU TEMPERATURE SENSING OF DEVICE UNDER TEST (DUT)

BACKGROUND

The present disclosure relates to environmental test systems and methods, and, in particular, to environmental test systems and methods in which temperature and humidity in an environmental chamber are controlled to eliminate condensation at or near the device under test (DUT).

In conventional humidity-controlled and temperature-controlled chamber systems, a device under test (DUT) can be subjected to various forms of testing regimens under various environments. In a large number of these testing regiments, it is important that condensation not be present at or near the DUT, to ensure accurate testing, prevent failure of or damage to the DUT, or for other reasons. In conventional testing systems, because of the thermal mass of the DUT, or other factors, the temperature of the DUT may be at a temperature that is below the dew point of the controlled chamber environment. As a result, condensation can form, which can result in a spoiled testing regimen.

SUMMARY

According to one aspect, the present disclosure is directed to an environmental chamber system in which a device under test (DUT) can be tested. The environmental chamber system includes an environmental chamber in which the DUT can be tested. A temperature sensor senses temperature of the DUT and generates a signal indicative of temperature of the DUT. A controller receives at least one input signal related to at least one of temperature and humidity in the chamber and receives the signal indicative of temperature of the DUT. The controller provides at least one control signal for adjusting at least one of temperature and humidity in the chamber, such that the temperature of the DUT is not below a dew point of an environment in the chamber in a region of the chamber near the DUT, such that condensation in the environment in the chamber in the region near the DUT does not occur.

In some exemplary embodiments, the controller comprises a mathematical filter.

In some exemplary embodiments, the at least one input signal comprises two input signals, the two input signals being indicative of humidity and temperature in the chamber.

In some exemplary embodiments, the at least one control signal adjusts heating in the chamber.

In some exemplary embodiments, the at least one control signal adjusts cooling in the chamber.

In some exemplary embodiments, the at least one control signal is generated to remove moisture from the chamber.

In some exemplary embodiments, the at least one control signal is generated to add moisture to the chamber.

In some exemplary embodiments, the temperature sensor contacts the DUT inside the chamber.

In some exemplary embodiments, the temperature sensor is an infrared temperature sensor, and the DUT is within a field of view of the infrared sensor.

In some exemplary embodiments, the infrared sensor is inside the chamber.

In some exemplary embodiments, the infrared sensor is outside the chamber.

According to another aspect, the present disclosure is directed to a method of testing a device under test (DUT). The method comprises: placing the DUT in an environmental chamber; sensing temperature of the DUT with a temperature sensor, the temperature sensor generating a first signal, the first signal being indicative of temperature of the DUT; sensing at least one of temperature and humidity inside the chamber and generating at least one second signal indicative of the at least one of temperature and humidity inside the chamber; and generating at least one control signal for adjusting at least one of temperature and humidity in the chamber, such that the temperature of the DUT is not below a dew point of an environment in the chamber in a region of the chamber near the DUT, such that condensation in the environment in the chamber in the region near the DUT does not occur, the at least one control signal being based on first signal and the at least one second signal.

In some exemplary embodiments, the at least one second signal comprises two signals, the two signals being indicative of humidity and temperature in the chamber.

In some exemplary embodiments, the at least one control signal adjusts heating in the chamber.

In some exemplary embodiments, the at least one control signal adjusts cooling in the chamber.

In some exemplary embodiments, the at least one control signal is generated to remove moisture from the chamber.

In some exemplary embodiments, the at least one control signal is generated to add moisture to the chamber.

In some exemplary embodiments, the temperature sensor contacts the DUT inside the chamber.

In some exemplary embodiments, the temperature sensor is an infrared temperature sensor, and the DUT is within a field of view of the infrared sensor.

In some exemplary embodiments, the infrared sensor is inside the chamber.

In some exemplary embodiments, the infrared sensor is outside the chamber.

BRIEF DESCRIPTION OF THE DRAWINGS

The foregoing and other features and advantages of the disclosure will be apparent from the more particular description of preferred embodiments, as illustrated in the accompanying drawings, in which like reference characters refer to the same parts throughout the different views. The drawings are not necessarily to scale, emphasis instead being placed upon illustrating the principles of the disclosure.

DETAILED DESCRIPTION

Figure 1:
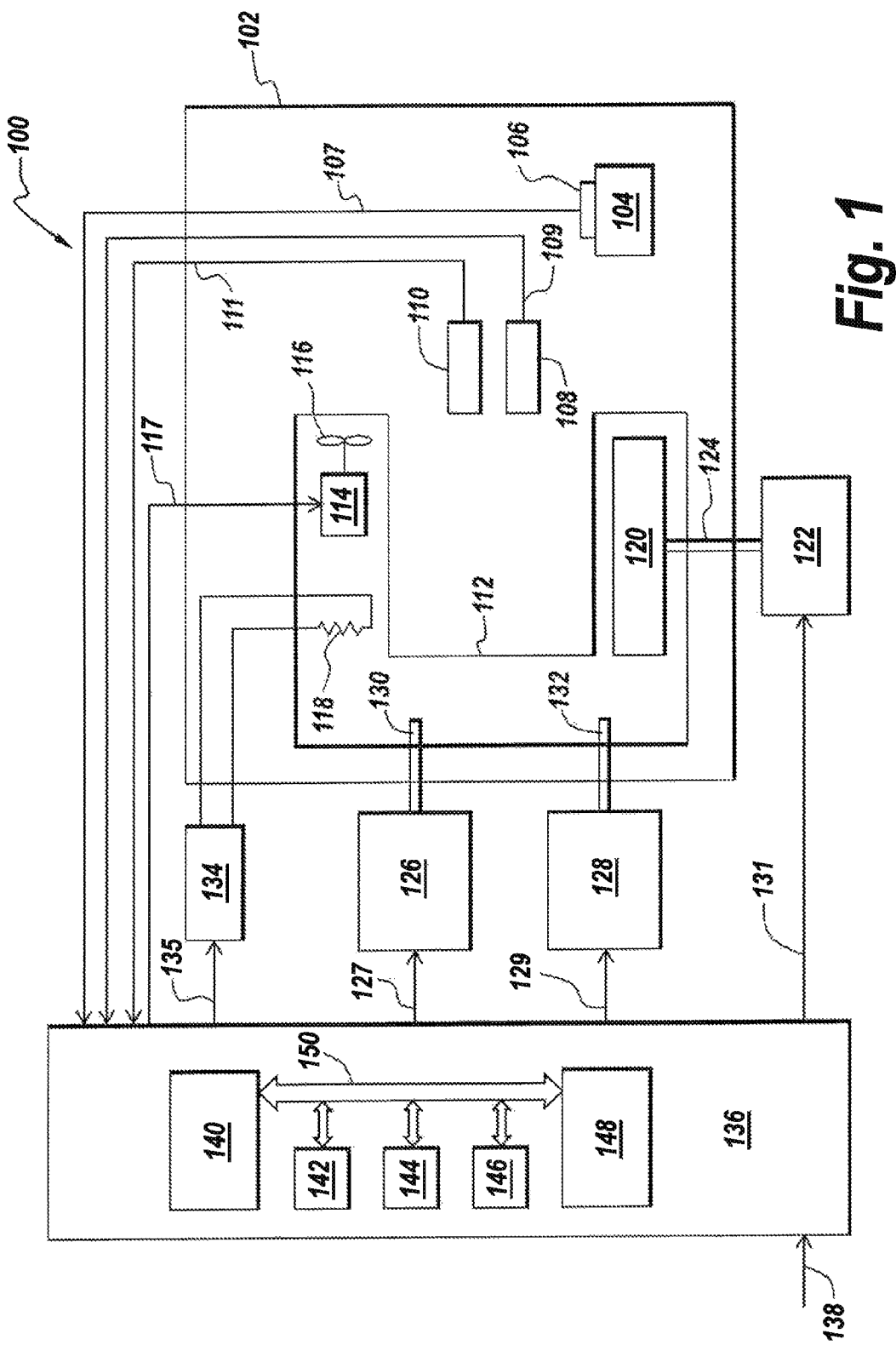
FIG. 1 contains a schematic block diagram of an environmental chamber system, according to some exemplary embodiments.

FIG. 1 contains a schematic block diagram of an environmental chamber system 100, according to some exemplary embodiments. Referring to FIG. 1, the system 100 includes an environmentally-controlled chamber 102 in which a device under test (DUT) 104 can be located such that a testing regimen can be carried out on the DUT in certain prescribed environments. For example, in the embodiment illustrated in FIG. 1, the temperature and humidity inside the chamber 102 is controllable. To that end, the system 100 includes a temperature sensor 110 and a humidity sensor 108 inside the chamber 102. The temperature sensor 110 and humidity sensor 108 sense the temperature and humidity, respectively, inside the chamber 102 and transfer signals indicative of the temperature and humidity, respectively, to a system controller 136.

The environment inside the chamber 102 is conditioned such as by adding and/or removing moisture and/or heating and/or cooling the environment using a mixing blower 116, which moves the chamber environmental gas, e.g., air, through a plenum 112 located inside the chamber 102. In general, rapid and turbulent air flow through the plenum 112 is achieved by the mixing blower 116, under the control of the mixing blower power and control unit 114, which is controlled by a control signal on signal line 117 from the system controller 136. The mixing blower 116 exhausts the flowing air into the chamber 102 to control the environment in the chamber 102.

The air in the chamber 102 is heated by heater 118. In some exemplary embodiments, the heater 118 is a resistive heater which operates under the control of the heater power and control unit 134, which is controlled by the system controller 136 via a control signal on signal line 135.

In some exemplary embodiments, the air in the camber 102 is cooled by, for example, an evaporator unit 120. Air from the chamber 102 is drawn into the plenum 112 by the mixing blower 116, where the evaporator 120 cools the air. The air entering the plenum 112 can be cooled by the evaporator 120 either mechanically, i.e., by a refrigeration cycle operating in concert with the evaporator 120, or cryogenically by the injection of a cryogenic material into the evaporator 120. In the exemplary embodiment illustrated in FIG. 1, the evaporator 120 cools the air by injection of a cryogenic material, which can be, for example, liquid nitrogen ($LN_2$), liquid carbon dioxide $LCO_2$, or other such material. The $LN_2$ or $LCO_2$ is transported from a source 122 through the wall of the chamber 102 via a pipe or tubing 124, and into the evaporator 120. The transport of the cooling material is controlled by the system controller 136 via a control signal on signal line 131 as shown in FIG. 1. As the injected material enters the evaporator 120, it evaporates, thus cooling the air flowing along the outer surface of the evaporator 120.

As noted above, in some exemplary embodiments, humidity in the chamber 102 is also controlled. Accordingly, the system 100 also includes a moisture input for adding humidity to the environment inside the chamber 102 and a drying input for removing humidity from the environment inside the chamber 102. In some exemplary embodiments, the moisture input may be, for example, atomized water, which is transported from a source 126 through the wall of the chamber 102 via a pipe or tubing 130, and into the plenum 112. The flow and/or the flow rate of the atomized water, and, therefore, the humidity adjustment made by the atomized water, is controlled by the system controller 136 via a control signal on signal line 127, as shown in FIG. 1. In some exemplary embodiments, the drying input may be, for example, dry nitrogen, which is transported from a source 128 through the wall of the chamber 102 via a pipe or tubing 132, and into the plenum 112. The flow and/or the flow rate of the dry nitrogen, and, therefore, the humidity adjustment made by the dry nitrogen, is controlled by the system controller 136 via a control signal on signal line 129, as shown in FIG. 1.

Either or both of the moisture input and the drying input are introduced into the turbulent air flow in the plenum 112. According to the disclosure, the system controller 136, via the appropriate control signals, sets the combination of the moisture input and the drying input as desired to achieve the desired humidity in the chamber 102, as measured by the humidity sensor 108. Similarly, either or both of the heating 118 and cooling 120 are introduced into the turbulent air flow in the plenum 112. According to the disclosure, the system controller 136, via the appropriate control signals, sets the combination of the heating input and cooling input as desired to achieve the desired temperature in the chamber 102.

The system 100 also includes a DUT temperature sensor 106 located in close proximity to and/or in contact with the DUT 104. The DUT temperature sensor 106 directly senses the temperature of the DUT 104 in situ, independent of any potential influence by any other factors, such as, for example, temperature variations/gradients in the chamber environment. The DUT temperature sensor 106 senses the temperature of the DUT 104 in situ and forwards a signal indicative of the temperature of the DUT 104 to the system controller 136 on signal line 107. In some exemplary embodiments, the DUT temperature sensor 106 can be or include a resistance to temperature (RTD) device, a thermocouple, a thermistor, or other such contact temperature sensing device.

The system controller 136 controls the operation of the system 100 by processing the various input signals it receives from the various sensors in the system and generating control signals using the input signals. In some exemplary embodiments, the system controller 136 includes a processing device 140, which can be a microprocessor, a microcontroller, a programmed gate array, or other such device. System controller 136 also includes memory circuits 142, 144, 146, each of which can be some form of random access memory (RAM) or some form of read-only memory (ROM) or some form of programmable read-only memory (PROM), or other memory device. One or more of the memory circuits 142, 144, 146 can store program instructions and data used by the system controller 136 to control the system 100. The system controller 136 also includes peripheral circuitry 148 associated with the processing device 140 and memories 142, 144, 146. The peripheral circuitry 148 may include, for example, input/output interface circuitry, mathematical operations circuitry, or other circuitry used to carry out the functions of the system controller 136 together with the processing device 140 and the memories 142, 144, 146. The processing device 140, the memories 142, 144, 146 and the peripheral circuitry 148 are connected via a system bus 150. Signals among the processing device 140, memories 142, 144, 146 and the peripheral circuitry 148 are carried over the system bus 150.

As described above, the system 100 operates to eliminate condensation at or near the DUT 104 during testing. This is achieved by obtaining an accurate in-situ measurement of the temperature of the DUT 104, via the DUT temperature sensor 106, in addition to accurate measurements of chamber humidity via the humidity sensor 108 and accurate measurements of chamber temperature via the temperature sensor 110. By directly sensing the actual temperature of the DUT 104 in situ, the system can make adjustments to the humidity and temperature in the chamber 102 to ensure that the temperature of the DUT 104 is not below the dew point of the air in the chamber 102, which eliminates condensation at or near the DUT 104.

The system controller 136, through the processing device 140, memories 142, 144, 146 and peripheral circuitry 148, controls the system 100 by executing a control process or function. In some exemplary embodiments, the control process or function can be or can include a mathematical filter. The control process or function receives as input variables the temperature of the DUT 104 via signal line 107, the temperature of the chamber 102 via signal line 111 and the humidity of the chamber 102 via signal line 109. The control process or function processes these received signals and produces a set of control signals to control the humidity and temperature of the chamber 102 such that condensation does not occur at or near the DUT 104.

Specifically, the control process or function generates a heating control signal on control signal line 135 to command heating as required via the heating power and control unit 134. The control signal can command the heater 118 between on and off states, or it may adjust the power supplied to the heater 118 to adjust the output heat. Similarly, the control process or function generates a cooling control signal on signal line 131 to command cooling as required via the cooling source 122. The control signal can command the source 122 between on and off states such that the flow of cryogenic material, e.g., $LN_2$ or $LCO_2$, switches between flowing and not flowing, or it may adjust the flow rate of the $LN_2$ or $LCO_2$ to adjust the cooling. Similarly, the control process or function generates a moisture control signal on signal line 127 to command the addition of moisture to the air in the chamber 102 as required via the moisture source 126. As noted above, the moisture source may be a source of atomized water. The control signal can command the source 126 between on and off states such that the flow of moisture, i.e., atomized water, switches between flowing and not flowing, or it may adjust the flow rate of the atomized water. Similarly, the control process or function generates a drying control signal on signal line 129 to command the reduction of moisture in the air in the chamber 102 as required via the drying source 128. As noted above, the drying source 128 may be a source of dry nitrogen. The control signal can command the source 128 between on and off states such that the flow of dry nitrogen switches between flowing and not flowing, or it may adjust the flow rate of the dry nitrogen. The control process or function also generates a control signal on signal line 117, which controls the mixing blower 116 via the mixing blower power and control unit 114, to control flow and mixture of the environmental gas, i.e., air, inside the chamber 102.

In some exemplary embodiments, the system controller 136 is also provided with an enable input on signal line 138. The enable input can be used to enable or disable the elimination of condensation at the DUT 104. The enable input can also be an adjustment signal which allows the user to set a desired or acceptable level of condensation at the DUT 104, rather than completely eliminating condensation. This acceptable level signal is used by the control process or function in generating the various control signals described in detail above such that the acceptable level of condensation is achieved.

Figure 2:
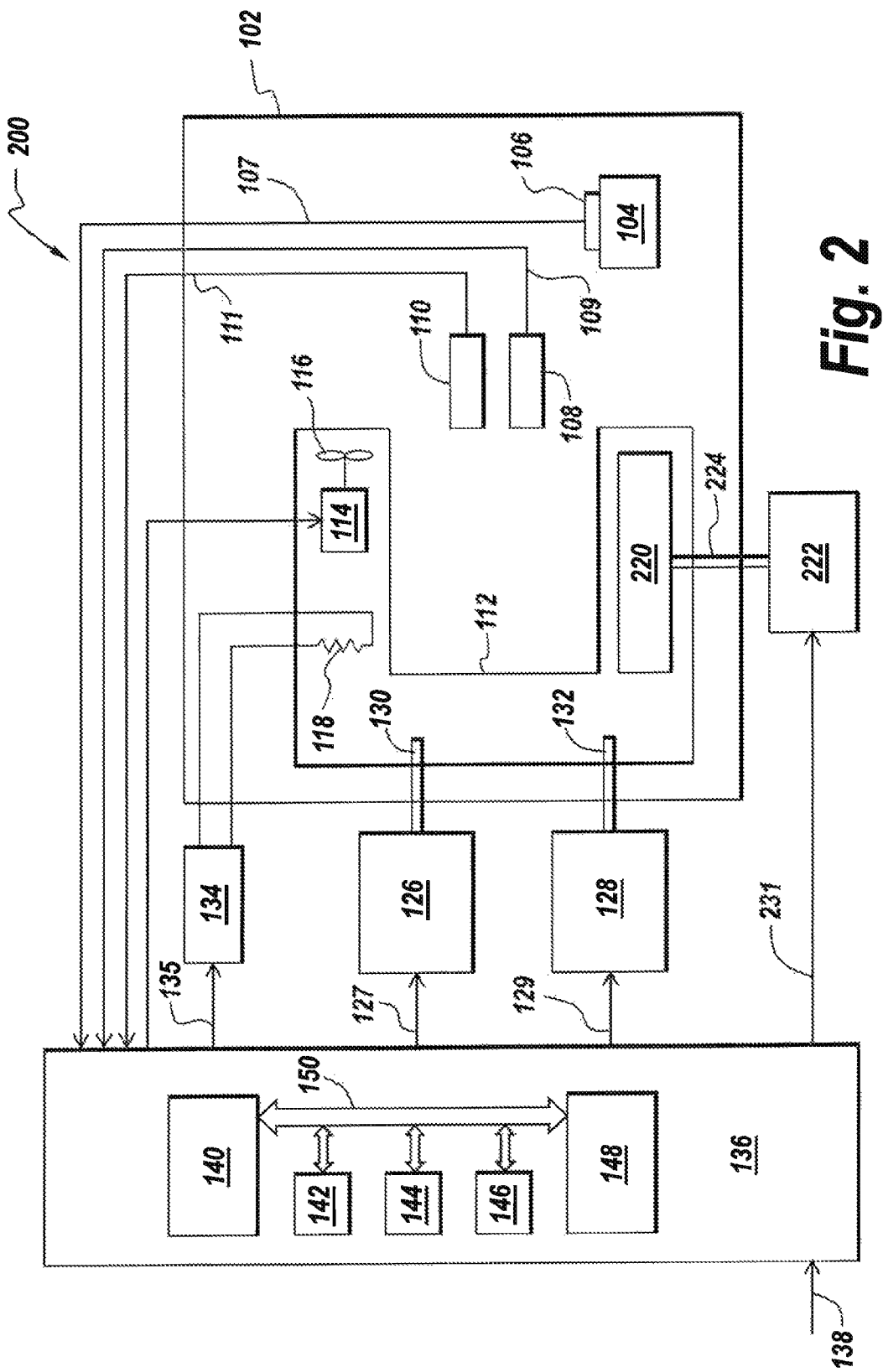
FIG. 2 contains a schematic block diagram of an environmental chamber system, according to other exemplary embodiments.

FIG. 2 contains a schematic block diagram of an environmental chamber system, according to other exemplary embodiments. The difference between the embodiments of FIG. 2 and the embodiments of FIG. 1 is that, in the embodiments of FIG. 1, cooling is achieved by injecting cryogenic material into the evaporator 120, whereas, in the embodiments of FIG. 2, the cooling is achieved by mechanical refrigeration, i.e., by a mechanical refrigeration cycle, and the evaporator 220 of the embodiments of FIG. 2 is part of the mechanical refrigeration cycle.

Elements, functions and processes of the embodiments of FIG. 2 that are the same as those of the embodiments of FIG. 1 are identified by like reference numerals. Detailed description of these like elements, functions and processes will not be repeated.

Referring to FIG. 2, in some exemplary embodiments, the air in the chamber 102 is cooled by, for example, an evaporator unit 220. Air from the chamber 102 is drawn into the plenum 112 by the mixing blower 116, where the evaporator 220 cools the air. In these embodiments, the air entering the plenum 112 is cooled by the evaporator 220 mechanically, i.e., by a refrigeration cycle operating in concert with the evaporator 220. The mechanical refrigeration cycle components are indicated generally by 222. Refrigerant in the refrigeration cycle is transported from the remainder of the refrigeration cycle 222 through the wall of the chamber 102 via a pipe or tubing 224, and into the evaporator 220. The transport of the refrigerant is controlled by the system controller 136 via a control signal on signal line 231 as shown in FIG. 2. As the refrigerant enters the evaporator 220, it evaporates, thus cooling the air flowing along the outer surface of the evaporator 220.

According to exemplary embodiments, the control process or function generates a cooling control signal on signal line 231 to command cooling as required via the refrigeration cycle 222. The control signal can command the cycle 222 between on and off states such that the flow of refrigerant switches between flowing and not flowing, or it may adjust the flow rate of the refrigerant to adjust the cooling.

In the embodiments described above, the DUT temperature sensor 106 is disclosed as being a contact temperature sensor in direct contact with or immediately adjacent to the DUT 104 such that temperature of the DUT 104 is sensed directly. According to the disclosure, other non-contact types of temperature sensors can be used to sense the temperature of the DUT 104 directly. For example, temperature of the DUT 104 may be sensed directly using an infrared temperature sensor, which can be located some distance from the DUT 104 and does not make contact with the DUT 104. The infrared temperature sensor of these embodiments may be located inside the chamber or outside the chamber.

FIGS. 3 through 6 are schematic block diagrams of environmental chamber systems which use remote sensors such as infrared temperature sensors to directly sense the temperature of the DUT 104. In any of the embodiments described herein, the infrared temperature sensor may be of the type manufactured and sold by Exergen Corporation of Watertown, Mass., USA. Other types of infrared temperature sensors may be used according to the disclosure. The sensed temperature of the DUT 104 is used as described in detail above to adjust temperature and/or humidity inside the chamber such that condensation at or near the DUT is eliminated or substantially reduced.

Figure 3:
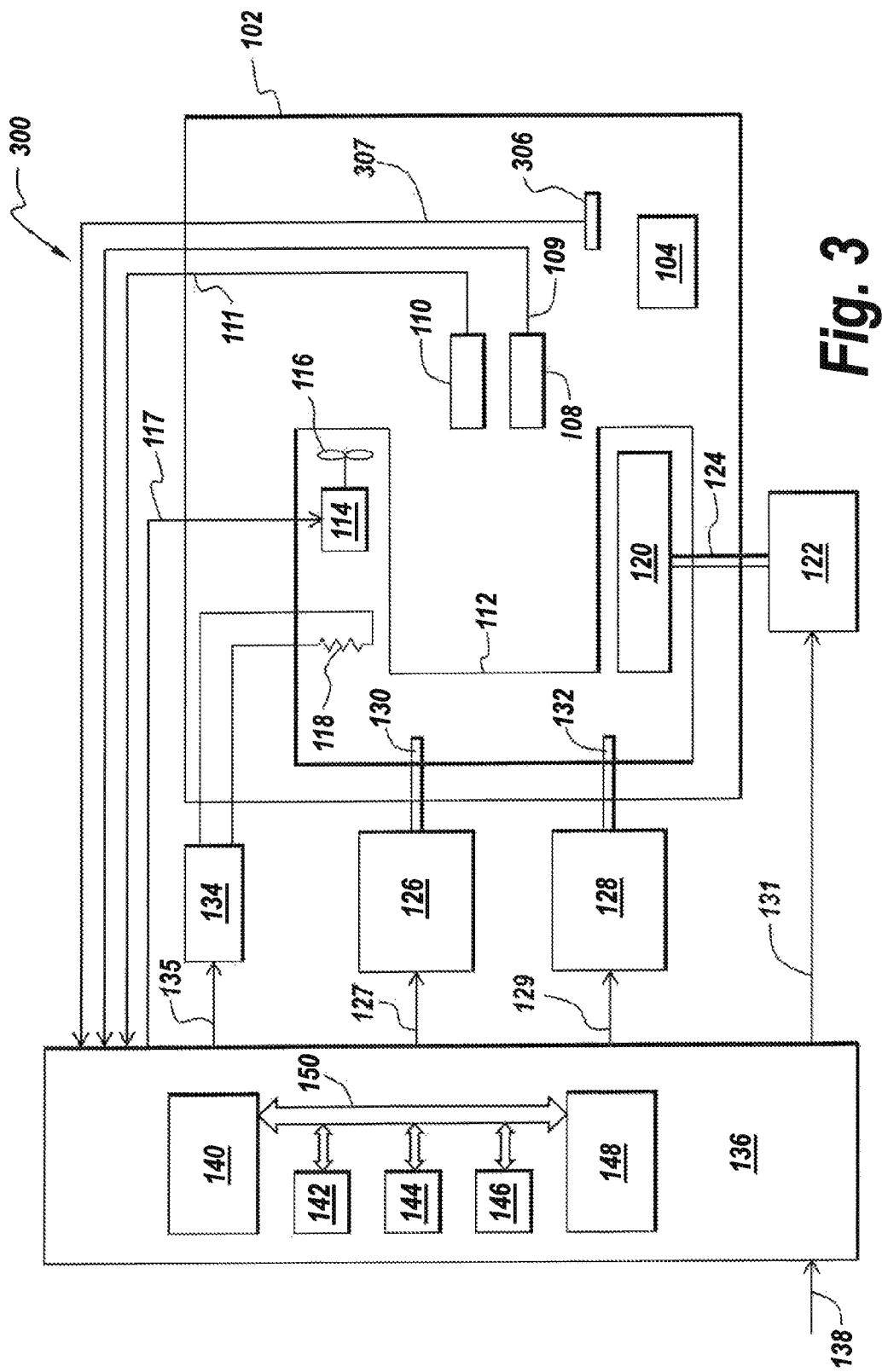
FIG. 3 contains a schematic block diagram of an environmental chamber system using a remote, non-contact DUT temperature sensor, according to other exemplary embodiments.

FIG. 3 contains a schematic block diagram of an environmental chamber system 300 using a remote, non-contact DUT temperature sensor 306, according to other exemplary embodiments. The chamber system 300 of FIG. 3 is the same as the chamber system 100 of FIG. 1 except that that chamber system 300 of FIG. 3 uses a remote, non-contact infrared DUT temperature sensor 306 instead of the contact temperature sensor 106 in the embodiment of FIG. 1. Elements of the embodiments of FIG. 3 that are the same as elements of the embodiments of FIG. 1 are identified by like reference numerals. Detailed description of these like elements will not be repeated.

Referring to FIG. 3, the infrared DUT temperature sensor 306 is positioned and directed such that the DUT 104 is within the field of view of the infrared DUT temperature sensor 306, such that the infrared DUT temperature sensor 306 directly senses the temperature of the DUT 104. The sensor 306 generates a signal indicative of the sensed temperature of the DUT 104 and forwards the signal on signal line 307 to the controller 136, which uses the signal as described above in detail to adjust temperature and/or humidity inside the chamber 102 such that condensation at or near the DUT 104 is eliminated or substantially reduced.

Figure 4:
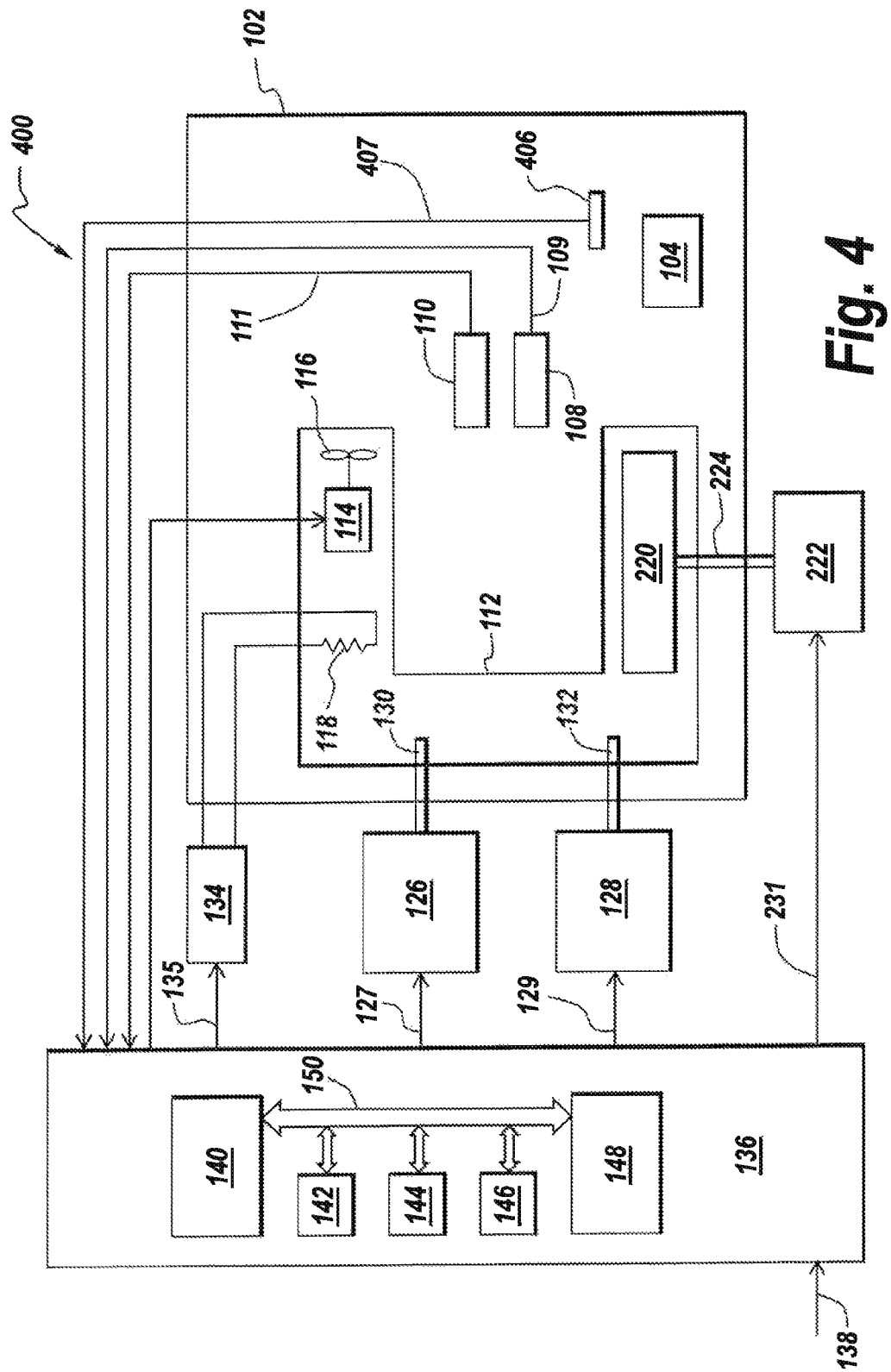
FIG. 4 contains a schematic block diagram of an environmental chamber system using a remote, non-contact DUT temperature sensor, according to other exemplary embodiments.

FIG. 4 contains a schematic block diagram of an environmental chamber system 400 using a remote, non-contact DUT temperature sensor 406, according to other exemplary embodiments. The chamber system 400 of FIG. 4 is the same as the chamber system 200 of FIG. 2 except that that chamber system 400 of FIG. 4 uses a remote, non-contact infrared DUT temperature sensor 406 instead of the contact temperature sensor 106 in the embodiment of FIG. 2. Elements of the embodiments of FIG. 4 that are the same as elements of the embodiments of FIG. 2 are identified by like reference numerals. Detailed description of these like elements will not be repeated.

Referring to FIG. 4, the infrared DUT temperature sensor 406 is positioned and directed such that the DUT 104 is within the field of view of the infrared DUT temperature sensor 406, such that the infrared DUT temperature sensor 406 directly senses the temperature of the DUT 104. The sensor 406 generates a signal indicative of the sensed temperature of the DUT 104 and forwards the signal on signal line 407 to the controller 136, which uses the signal as described above in detail to adjust temperature and/or humidity inside the chamber 102 such that condensation at or near the DUT 104 is eliminated or substantially reduced.

Figure 5:
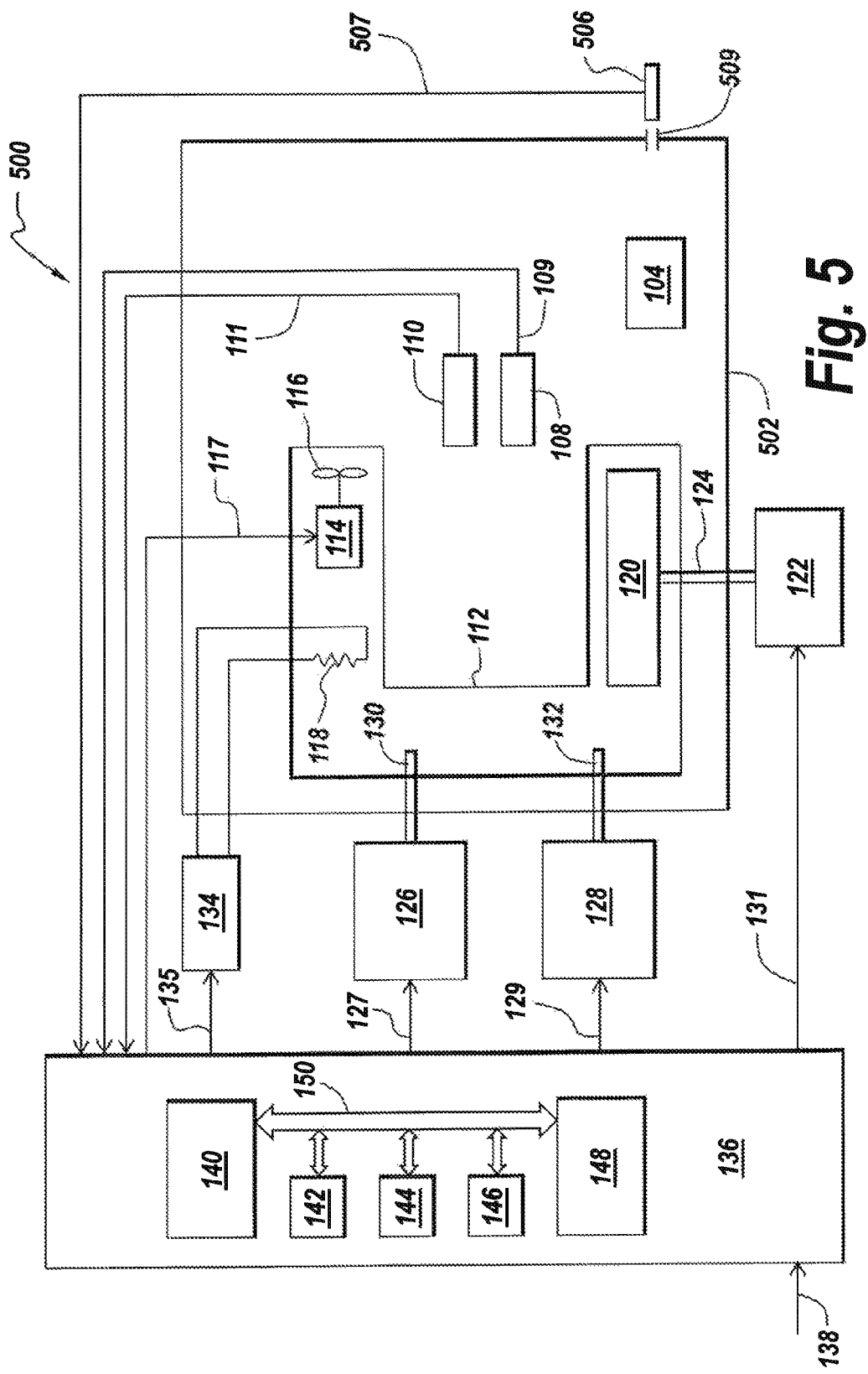
FIG. 5 contains a schematic block diagram of an environmental chamber system using a remote, non-contact DUT temperature sensor, according to other exemplary embodiments.

FIG. 5 contains a schematic block diagram of an environmental chamber system 500 using a remote, non-contact DUT temperature sensor 506, according to other exemplary embodiments. The chamber system 500 of FIG. 5 is the same as the chamber system 300 of FIG. 3 except that, in the chamber system 500 of FIG. 5, the remote non-contact infrared DUT temperature sensor 506 is outside the chamber 502, in contrast to the system 300 of FIG. 3 in which the infrared DUT temperature sensor 306 is inside the chamber 102. Elements of the embodiments of FIG. 5 that are the same as elements of the embodiments of FIG. 3 are identified by like reference numerals. Detailed description of these like elements will not be repeated.

Referring to FIG. 5, the infrared DUT temperature sensor 506 is positioned and directed such that the DUT 104 is within the field of view of the infrared DUT temperature sensor 506 through an infrared-transparent window 509 in the chamber 502, such that the infrared DUT temperature sensor 506 directly senses the temperature of the DUT 104. The sensor 506 generates a signal indicative of the sensed temperature of the DUT 104 and forwards the signal on signal line 507 to the controller 136, which uses the signal as described above in detail to adjust temperature and/or humidity inside the chamber 502 such that condensation at or near the DUT 104 is eliminated or substantially reduced.

Figure 6:
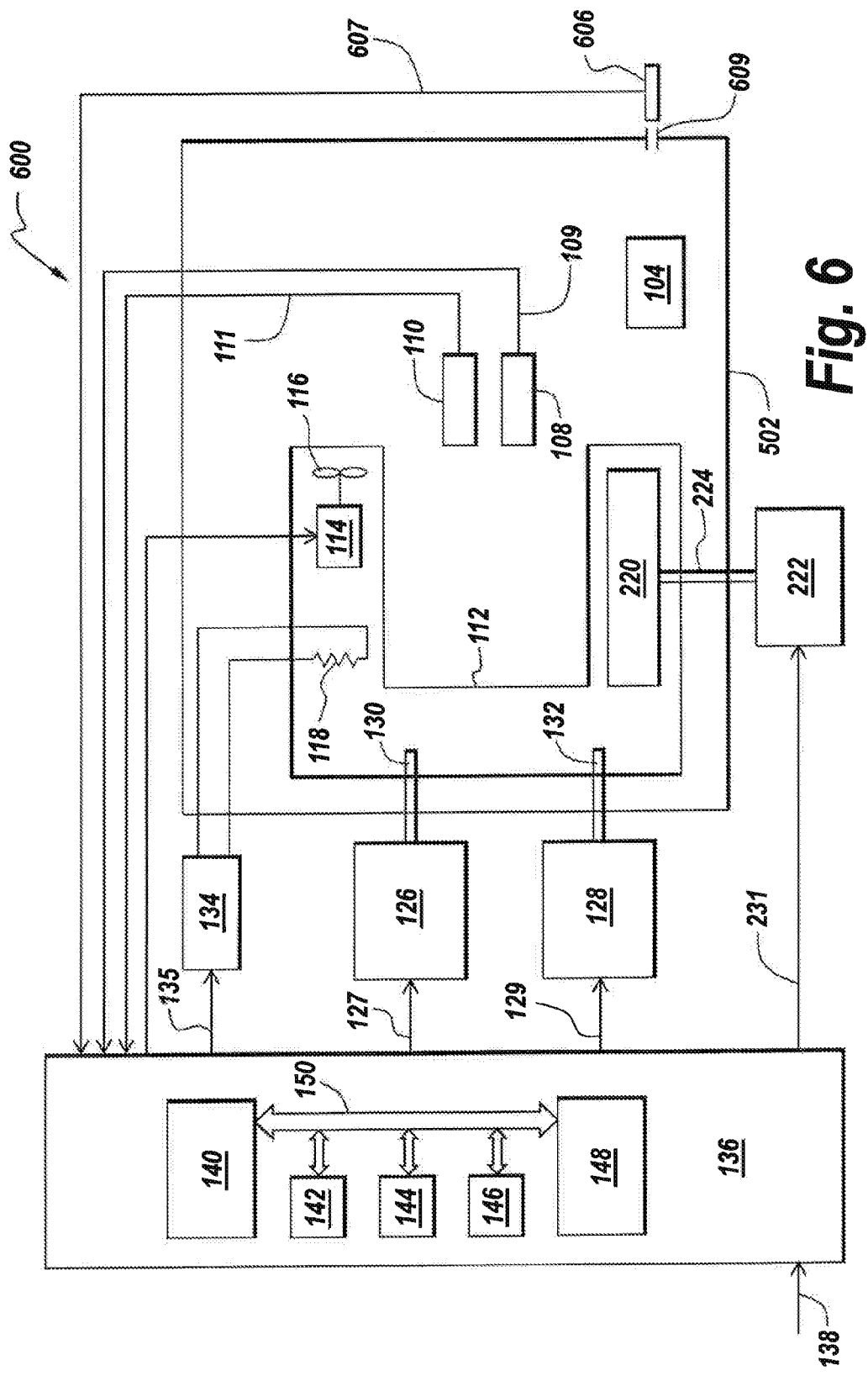
FIG. 6 contains a schematic block diagram of an environmental chamber system using a remote, non-contact DUT temperature sensor, according to other exemplary embodiments.

FIG. 6 contains a schematic block diagram of an environmental chamber system 600 using a remote, non-contact DUT temperature sensor 606, according to other exemplary embodiments. The chamber system 600 of FIG. 6 is the same as the chamber system 400 of FIG. 4 except that, in the chamber system 600 of FIG. 6, the remote non-contact infrared DUT temperature sensor 606 is outside the chamber 602, in contrast to the system 400 of FIG. 4 in which the infrared DUT temperature sensor 406 is inside the chamber 102. Elements of the embodiments of FIG. 6 that are the same as elements of the embodiments of FIG. 4 are identified by like reference numerals. Detailed description of these like elements will not be repeated.

Referring to FIG. 6, the infrared DUT temperature sensor 606 is positioned and directed such that the DUT 104 is within the field of view of the infrared DUT temperature sensor 606 through an infrared-transparent window 609 in the chamber 602, such that the infrared DUT temperature sensor 606 directly senses the temperature of the DUT 104. The sensor 606 generates a signal indicative of the sensed temperature of the DUT 104 and forwards the signal on signal line 607 to the controller 136, which uses the signal as described above in detail to adjust temperature and/or humidity inside the chamber 602 such that condensation at or near the DUT 104 is eliminated or substantially reduced.

Combinations of Features

Various features of the present disclosure have been described above in detail. The disclosure covers any and all combinations of any number of the features described herein, unless the description specifically excludes a combination of features. The following examples illustrate some of the combinations of features contemplated and disclosed herein in accordance with this disclosure.

In any of the embodiments described in detail and/or claimed herein, the controller can include a mathematical filter.

In any of the embodiments described in detail and/or claimed herein, at least one input signal can include two input signals, the two input signals being indicative of humidity and temperature in the chamber.

In any of the embodiments described in detail and/or claimed herein, at least one control signal can adjust heating in the chamber.

In any of the embodiments described in detail and/or claimed herein, at least one control signal can adjust cooling in the chamber.

In any of the embodiments described in detail and/or claimed herein, at least one control signal can be generated to remove moisture from the chamber.

In any of the embodiments described in detail and/or claimed herein, at least one control signal can be generated to add moisture to the chamber.

In any of the embodiments described in detail and/or claimed herein, the temperature sensor can contact the DUT inside the chamber.

In any of the embodiments described in detail and/or claimed herein, the temperature sensor can be an infrared temperature sensor, and the DUT can be within a field of view of the infrared sensor.

In any of the embodiments described in detail and/or claimed herein, the infrared sensor can be inside the chamber.

In any of the embodiments described in detail and/or claimed herein, the infrared sensor can be outside the chamber.

While the present disclosure has made reference to exemplary embodiments, it will be understood by those of ordinary skill in the art that various changes in form and details may be made therein without departing from the spirit and scope of the present disclosure as defined by the following claims.

The invention claimed is:

1. An environmental chamber system in which a device under test (DUT) can be tested, the environmental chamber system comprising:
   an environmental chamber in which the DUT can be tested;
   a temperature sensor for sensing temperature of the DUT, the temperature sensor generating a signal indicative of temperature of the DUT, the temperature sensor being an infrared temperature sensor located outside the chamber, the DUT being within a field of view of the infrared temperature sensor; and a controller for receiving at least one input signal related to at least one of temperature and humidity in the chamber and receiving the signal indicative of temperature of the DUT and providing at least one control signal for adjusting at least one of temperature and humidity in the chamber, such that the temperature of the DUT is not below a dew point of an environment in the chamber in a region of the chamber near the DUT, such that condensation in the environment in the chamber in the region near the DUT does not occur.

2. The system of claim 1, wherein the controller comprises a mathematical filter.

3. The system of claim 1, wherein the at least one input signal comprises two input signals, the two input signals being indicative of humidity and temperature in the chamber.

4. The system of claim 1, wherein the at least one control signal adjusts heating in the chamber.

5. The system of claim 1, wherein the at least one control signal adjusts cooling in the chamber.

6. The system of claim 1, wherein the at least one control signal is generated to remove moisture from the chamber.

7. The system of claim 1, wherein the at least one control signal is generated to add moisture to the chamber.

8. A method of testing a device under test (DUT), comprising:

placing the DUT in an environmental chamber;

sensing temperature of the DUT with a temperature sensor, the temperature sensor generating a first signal, the first signal being indicative of temperature of the DUT, the temperature sensor being an infrared temperature sensor located outside the environmental chamber, the DUT being within a field of view of the infrared temperature sensor;

sensing at least one of temperature and humidity inside the chamber and generating at least one second signal indicative of the at least one of temperature and humidity inside the chamber; and generating at least one control signal for adjusting at least one of temperature and humidity in the chamber, such that the temperature of the DUT is not below a dew point of an environment in the chamber in a region of the chamber near the DUT, such that condensation in the environment in the chamber in the region near the DUT does not occur, the at least one control signal being based on the first signal and the at least one second signal.

9. The method of claim 8, wherein the at least one second signal comprises two signals, the two signals being indicative of humidity and temperature in the chamber.

10. The method of claim 8, wherein the at least one control signal adjusts heating in the chamber.

11. The method of claim 8, wherein the at least one control signal adjusts cooling in the chamber.

12. The method of claim 8, wherein the at least one control signal is generated to remove moisture from the chamber.

13. The method of claim 8, wherein the at least one control signal is generated to add moisture to the chamber.

* * * * *